United States Patent

Frigola-Constansa et al.

[11] Patent Number: 5,444,059
[45] Date of Patent: Aug. 22, 1995

[54] 2-(4-AZOLYLBUTYL)-1-PIPERAZINYL)-5-HYDROXY-PYRIMIDINE DERIVATIVES, THEIR PREPARATION AND THEIR APPLICATION AS MEDICINAL PRODUCTS

[75] Inventors: Jordi Frigola-Constansa; Ramon Merce-Vidal, both of Barcelona, Spain

[73] Assignee: Laboratorios Del. Dr. Esteve, S.A., Barcelona, Spain

[21] Appl. No.: 192,142

[22] Filed: Feb. 4, 1994

[30] Foreign Application Priority Data

Feb. 5, 1993 [FR] France .................. 93 01293

[51] Int. Cl.⁶ .................. C07D 403/14; A61K 31/495
[52] U.S. Cl. .................. 514/252; 544/295
[58] Field of Search .................. 544/298, 295; 514/273, 514/252

[56] References Cited

U.S. PATENT DOCUMENTS

| | | | |
|---|---|---|---|
| 4,423,049 | 12/1983 | Temple | 514/252 |
| 4,818,756 | 4/1989 | Seidel et al. | 514/234.5 |
| 4,937,343 | 6/1990 | Seidel et al. | 544/295 |
| 4,988,809 | 1/1991 | Seidel et al. | 544/285 |
| 5,128,343 | 7/1992 | Pinol et al. | 514/252 |
| 5,162,323 | 11/1992 | Frigola-Constansa et al. | 514/252 |
| 5,180,726 | 1/1993 | Carlier et al. | 514/252 |
| 5,182,280 | 1/1993 | Cuberer-Altisent et al. | 514/252 |
| 5,182,281 | 1/1993 | Frigola-Constansa et al. | 514/252 |
| 5,187,276 | 2/1993 | Siedel et al. | 544/284 |

FOREIGN PATENT DOCUMENTS

| | | |
|---|---|---|
| 0129128A2 | 12/1984 | European Pat. Off. . |
| 0129128 | 12/1984 | European Pat. Off. . |
| 0382637 | 8/1990 | European Pat. Off. . |
| 0382637A1 | 8/1990 | European Pat. Off. . |
| 3248160 | 7/1987 | Germany . |

*Primary Examiner*—Joseph E. Evans
*Attorney, Agent, or Firm*—Dressler, Goldsmith, Shore & Milnamow, Ltd.

[57] ABSTRACT

2-[4-(4-azolylbutyl)-1-piperazinyl]-pyrimidine derivatives characterized in that they correspond to the general formula I

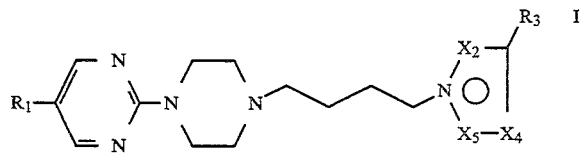

in which $X_2$ represents a nitrogen atom or a $C-R_2$ group, $X_4$ represents a nitrogen atom or a $C-R_4$ group, $X_5$ represents a nitrogen atom or a $C-R_5$ group, the process for preparing them, their application as medicinal product, and the pharmaceutical compositions containing them.

4 Claims, No Drawings

2-(4-AZOLYLBUTYL)-1-PIPERAZINYL)-5-HYDROXY-PYRIMIDINE DERIVATIVES, THEIR PREPARATION AND THEIR APPLICATION AS MEDICINAL PRODUCTS

The present invention relates to new 2-[4-(4-azolylbutyl)-1-piperazinyl] derivatives of general formula I, to the process for preparing them, to their application as medicinal products and to the pharmaceutical compositions containing them,

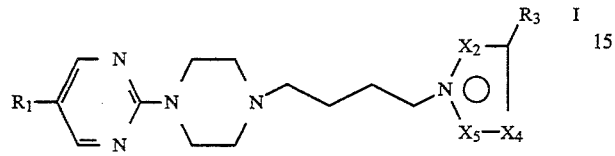

where $R_1$ represents a hydroxyl radical, $X_2$ represents a nitrogen atom or a C-$R_2$ group, $X_4$ represents a nitrogen atom or a C-$R_4$ group, $X_5$ represents a nitrogen atom or a C-$R_5$ group, and $R_2$, $R_3$, $R_4$ and $R_5$, which are identical or different, represent a hydrogen atom, a halogen, a lower alkyl radical, a nitro radical, a hydroxy radical, an alkoxy radical, a cyano radical, a carboxylic radical, a carboxamide radical, an alkyl carboxylate radical, an aryl radical, a sulphonamido radical, an amino or substituted amino radical.

The alkyl groups of the above radicals are preferably linear or branched $C_1$–$C_6$ lower alkyl groups. Aryl should preferably be understood to mean an optionally substituted phenyl radical or an aromatic heterocycle comprising 5 to 6 members and at least one nitrogen atom.

The compounds which are the subject of the invention can be used in the pharmaceutical industry as intermediate synthesis products for the preparation of medicinal products.

Various cyclic amides with anxiolytic activity have been known for the past few years, which are derived from arylpiperazines of general formula II

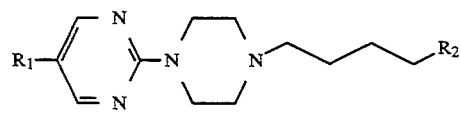

such as: Buspirone (Drugs of the Future, 1976, 1, 409); Gepirone (Drugs of the Future, 1985, 10, 456); Ipsapirone (Drugs of the Future, 1986, 11, 565); and Tandospirone (Drugs of the Future, 1989, 14, 1148) in which $R_2$ represents a hydrogen atom and $R_2$ is indicated below for each of them

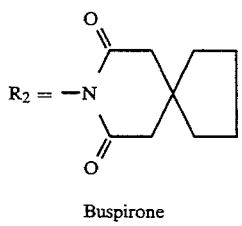

Buspirone

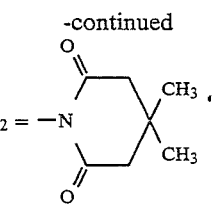

Gepirone

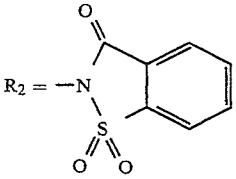

Ipsapirone

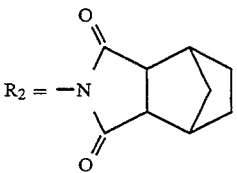

Tandospirone

There has also been found, in our laboratory, a series of aryl (o-heteroaryl)piperazinylalkylazoles which are useful as non-benzodiazepine agents for the treatment of anxiety (European Patents Nos. EP 382637, 497659 and 502786). In addition, these compounds are also useful for the treatment of other behavioural disorders (European Patents Nos. EP 429360 and 497658). Some of the most valuable compounds are azoles substituted in position 1 by a pyrimidinylpiperazinylbutyl group of formula I in which $R_1$ represents a hydrogen atom and $X_2$, $X_4$, $X_5$, $R_2$, $R_3$, $R_4$ and $R_5$ have the meanings indicated above.

A compound which is particularly suitable is Lesopitron (E-4424), a compound of general formula I in which $R_1$ represents a hydrogen atom, $X_2$ represents a $CR_2$ group, $X_4$ represents a $CR_4$ group, $X_5$ represents a nitrogen atom, $R_2$ and $R_4$ represent a hydrogen, and $R_3$ represents a chlorine. It has been shown that Lesopitron is a compound which has a very advantageous activity profile and which is much more potent than Buspirone or Ipsapirone (cf. B. Costall et al. J. Pharmacol. Experimental Therapeutics, 1992, 262, 90).

It has been said that the compounds of general formula II undergo a biotransformation "in vivo" to give rise essentially to two types of metabolites. One of the metabolites is the pyrimidylpiperazine of formula III

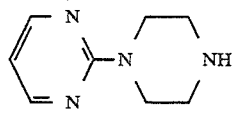

which compound has proved to be active both from a biochemical and pharmacological point of view, as has been described in numerous scientific publications of which the following will be cited as examples: E. Tatarczynska et al. Pol. J. Pharmacol Pharm. 1989, 41, 51; A. Diaz-Marot et al. J. Chromatogr. 1989, 490, 470; S.

Caccia et al. Acta Pharm. Jugosl. 1990, 40, 441; H. Nocon et al. J. Pharm. Pharmacol. 1990, 42, 642.

Another metabolite of the previously-mentioned compounds of general formula II is the corresponding 5-hydroxy derivative of general formula II in which $R_1$ represents a hydroxyl radical and $R_2$ has the meanings given above. Contrary to what occurs with compound III it has clearly been demonstrated that the compounds of general formula II in which $R_1$ represents a hydroxyl radical are biologically inactive. This behaviour is that which is usually observed when aromatic compounds are hydroxylated in a metabolic process (of for example: "Drug Metabolism. Chemical and Biochemical Aspects" B. Testa and P. Jenner, Marcel Dekker Inc., New York 1976). The following can be mentioned as references relating to the biological inactivity of compounds II in which $R_1$ represents a hydroxyl radical and R, has the meanings indicated above: R. E. Gammans, et al. The American Journal of Medicine, 1986, 80(3B), 41; C. P. Vander Maelen et al. Eur. J. Pharmacol., 1986, 129, 123; K. Ishizumi et al. Chem. Pharm. Bull., 1991, 39, 228; H. K. Jajoo, Drug Metabolism & Disposition, 1989, 17, 625 H. K. Jajoo, Drug Metabolism & Disposition, 1989, 17, 634.

It has now been discovered that the new 2-[4-(4-azolylbutyl)-1-piperazinyl]-5-hydroxypyrimidine derivatives of general formula I in which $R_1$ represents a hydroxyl radical, and $X_2$, $X_4$, $X_5$, $R_2$, $R_3$, $R_4$ and $R_5$ have the meanings indicated earlier, and which are the subject of the invention, are metabolites of the compounds described in the previous patents by the Applicants (EP 382 637 and EP 497 659) and, surprisingly, exhibit a biological activity on the central nervous system, in particular an anxiolytic and tranquillizer activity, which makes it possible to use them in therapy for the treatment of diseases affecting the central nervous system of mammalians.

The new derivatives of the general formula I in which $R_1$ represents a hydroxyl group and $X_2$, $X_4$, $X_5$, $R_2$, $R_3$, $R_4$ and $R_5$ have the meanings indicated earlier, can be prepared, according to the invention, by the following reaction scheme:

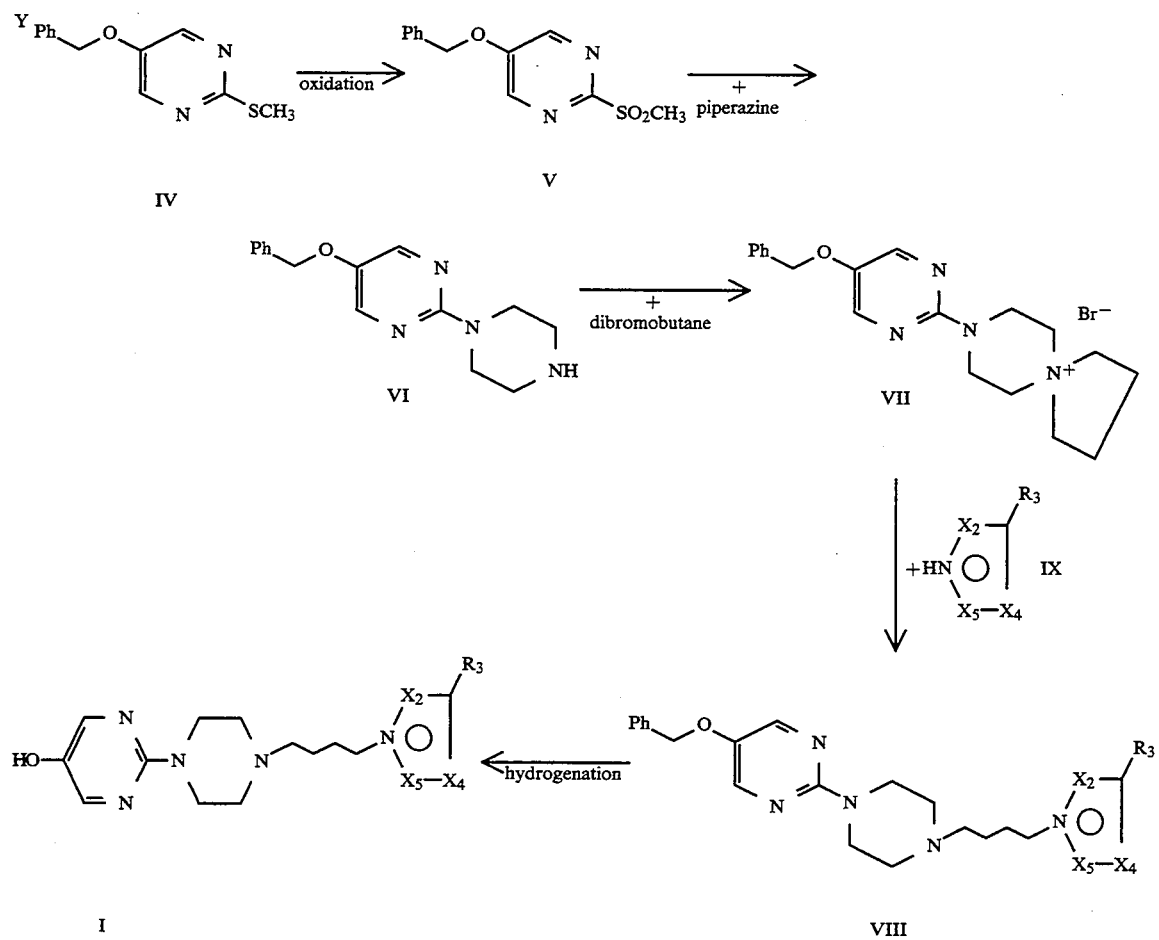

The starting material is 5-benzyloxy-2-methyl-thiopyrimidine IV, which can be prepared from benzyloxyacetyl chloride, by a sequence of reactions described by J. H. Chesterfield et al. J. Chem. Soc., 1960, 4590 and D. T. Hurst et al. J. Chem. Soc., 1965, 7116.

Compound V

Preparation of 5-benzyloxy-2-methylsulphonyl pyrimidine.

15.76 g (67.9 mmol) of 5-benzyloxy-2-thiomethyl-pyrimidine in 240 ml of chloroform are added to a solution of 46.88 g (135.8 mmol) of 50% m-chloroperbenzoic acid in water. The mixture is refluxed for 5 hours, it is cooled and a saturated sodium hydrogen carbonate solution is added. The organic phase is dried over sodium sulfate and evaporated to dryness, using 17.9 g (100%) of 5-benzyloxy-2-methylsulphonylpyrimidine.

Spectroscopic data. IR (KBr): 1125, 1300 cm$^{-1}$.

$^1$H NMR, (σ, CDCl$_3$): 8.58 (s, 2H); 7.41 (a.c., 5H); 5.27 (s, 2H); 3.30 (s, 3H).

Compound VI

Preparation of 5-benzyloxy-2-piperazinylpyrimidine.

A solution of 26.36 g (99.8 mmol) [lacuna] and 85 g (99.8 mmol) of piperazine in 185 ml of toluene is refluxed for 3 hours. It is allowed to cool, filtered and concentrated. 19.84 g (73%) of 5-benzyloxy-2-piperazinylpyrimidine crystallize from the solution. A sample recrystallized from hexane has a melting point of 86°-91° C.

Spectroscopic data-IR (KBr): 1267, 144 cm$^{-1}$.

$^1$H NMR, (σ, CDCl$_3$): 8.11 (s. 2H); 7.36 (a.c. 5H); 5.00 (s, 2H); 3.67 (t, 4H); 2.90 (t, 4H).

Compound VII

Preparation of 8 -(5-benzyloxy-2-pyrimidinyl) -8-aza-5-azoniaspiro [4.5]decane.

A solution of 7.25 g (26.85 mmol) of 5-benxyloxy-2-piperazinylpyrimidine and 3.2 ml (26.85 mmol) of 1,4-dibromobutane in 240 ml of chloroform and 7.42 g (53.7 mmol) of potassium carbonate is refluxed for 8 hours. It is cooled, filtered, evaporated to dryness and stirred with ethyl ether, yielding 16.0 g (91%) of 8-(5-benzyloxy-2-pyrimidinyl) -8-aza-5-azoniaspiro [4.5]decane bromide with a melting point of 128°-133° C.

Spectrascopic data-IR (KBr): 1268, 1451 cm$^{-1}$.

$^1$H NMR (σ, CDCl$_3$ ): 8.13 ( s, 2H), 7.38 ( a.c., 5H); 5.03 (s, 2H); 4.01 (a.c., 8H); 3.77 (t, 4H); 2.35 (t, 4H).

Compound VIII

Preparation of 2-{4-[4-(azol-1-yl)butyl]-1-piperazinyl}-5-benzyloxypyrimidine.

By reacting 8-(5-benzyloxy-2-pyrimidinyl-8-aza -5-azoniaspiro[4.5]decane bromide of formula VII with an azole of general formula IX

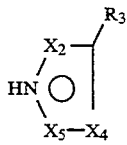

in which X$_2$ represents a nitrogen atom or a C-R$_2$ group, X$_4$ represents a nitrogen atom or a C-R$_4$ group, X$_5$ represents a nitrogen atom or a C-R$_5$ group, and R$_2$, R$_3$, R$_4$ and R$_5$, which are identical or different, represent a hydrogen atom, a halogen, a lower alkyl radical, a nitro radical, a hydroxy radical, an alkoxy radical, a cyano radical, a carboxylic radical, a carboxamide radical, an alkyl carboxylate radical, an aryl radical, a sulfonamide radical, an amino or substituted amino radical, a compound of general formula VIII is obtained in which X$_2$, X$_4$, X$_5$, R$_2$, R$_3$, R$_4$ and R$_5$ have the meanings given earlier. The reaction is carried out in a solvent with a high boiling point and in the presence of an organic or inorganic base.

Compounds I

Preparation of 2-{4-[4-(azol-1-yl)butyl]-1-piperazinyl}-5-hydroxypyrimidine.

A compound of general formula I is obtained by catalytic hydrogenation of a compound of general formula VIII. In both compounds, X$_2$, X$_4$, X$_5$, R$_2$, R$_3$, R$_4$ and R$_5$ have the meanings given earlier. The reaction is carried out in a solvent such as an alcohol, at temperatures of between 15° and 60° C., at pressures of between 1 and 15 atmospheres.

In the following examples, the preparation of new derivatives according to the invention is indicated. The examples which are presented below, given merely as illustration, should not however limit the scope of the invention in any manner.

EXAMPLE 1

Preparation of 2-{4-[4-(4-chloropyrazol-1-yl)butyl]-1-piperazinyl}-5-hydroxypyrimidine.

A mixture of 12.55 g (30.94 mmol) of 8-(5-benzyloxy-2-pyrimidinyl)-8-aza-5-azoniaspiro [4.5]decane bromide, 3.48 g (34.03 mols) of 4-chloropyrazole and 8.54 g (61.89 mmols) of potassium carbonate in 250 ml of dimethylformamide is refluxed for 12 hours and filtered off hot. The dimethylformamide is evaporated off and the product is chromatographed on silica gel, yielding 6.82 g (51.6%) of 2-{4-[4-(4-chloropyrazol-1-yl)butyl]-1-piperazinyl}-5-benzyloxypyrimidine.

Spectroscopic data.-IR (KBr): 1256, 1270, 1363, 1447, 1482 cm$^{-1}$.

RMN-$^1$H (σ, CDCl$_3$): 8.11 (s, H$_2$); 7.40 (s, 1H); 7.38 (a.c., 5H); 7.27 (s, 1H); 5.02 (s, 2H); 4.11 (t, 2H); 3.73 (m, 4H); 2.48 (m, 4H); 2.38 (t, 2H); 1.89 (quint. 2H); 1.52 ( quint., 2H).

A mixture of 6.87 g (16.07 mmol) of 2-{4-[4-(4-chloropyrazol-1-yl)butyl ]-1-piperazinyl}-5-benzyloxypyrimidine and 0.63 g of 10% palladium on carbon in 160 ml of ethanol is stirred for 12 hours under a hydrogen atmosphere at room temperature (24° C.) and at a pressure of 2 atmospheres. After filtration, washing with ethanol and evaporation to dryness, the product is chromatographed on silica gel, yielding 2.65 g (49%) of 2-{4-[4-(4-chloropyrazol-1-yl ) butyl]-1-piperazinyl}-5-hydroxypyrimidine with a melting point of 131°-2° C.

Spectroscopic data: IR (KBr):1258, 1271, 1364, 1428 cm$^{-1}$.

RMN-$^1$H (σ, CDCl$_3$): 7.99 (s, 2H); 7.40 (s, 1H); 7.36 (s, 1H); 4.06 (t, 2H); 3.66 (t, 4H); 2.49 (t, 4H); 2.37 (t, 2H); 1.84 (quint., 2H); 1.49 (quint., 2H).

EXAMPLE 2

Preparation of 2-{4-[4-(4,5-dichloro-2-methylimidazol-1-yl)butyl]-1-piperazinyl}-5-hydroxypyrimidine.

A mixture of 3.59 g (8.85 mmol) of 8-(5-benzyloxy-2-pyrimidinyl)-8-aza-5-azoniaspiro [4.5]decane bromide, 1.47 g (9.73 mmol) of 4,5-dichloro-2-methylimidazole and 4.89 g (35.41mmol) of potassium carbonate in 72 ml of dimethylformamide is refluxed for 12 hours and filtered hot. The dimethylformamide is evaporated and the product is chromatographed on silica gel, yielding 2.90 g (69%) of 2-{4-[4-(4,5-dichloro-2-methylimidazol-1-yl)butyl]-1-piperazinyl}-5-benzyloxypyrimidine.

Spectroscopic data: IR (KBr): 1033, 1050, 1231, 1412, 1580 cm$^{-1}$.

RMN-$^1$H (σ, CDCl$_3$): 8.11 (s, 2H); 7.37 (a.c., 5H); 5.01 (s, 2H); 3,80 (t, 2H); 3.72 (m, 4H); 2.48 (m, 4H); 2.36 (t, 2H); 2.36 (s, 3H); 1.65 (m, 4H).

A mixture of 2.90 g (6.10 mmol) of 2-{4-[4-(4,5-dichloro-2-methylimidazol-1-yl )butyl]-1-piperazinyl}-5-benzyloxypyrimidine and 0.30 g of 10% palladium on carbon in 50 ml of methanol is stirred for 12 hours under a hydrogen atmosphere at room temperature (24° C.) and at a pressure of 0.28 MPa. After filtration, washing with methanol and evaporation to dryness, the product is chromatographed on silica gel, yielding 1.39 g (59%) of 2-{4-[4-(4,5-dichloro-2-methylimidazol-1-yl)butyl]-1-piperazinyl}-5-hydroxypyrimidine with a melting point of 154°–6° C.

Spectroscopic data: IR (KBr): 1250, 1277, 1355, 1408, 1429, 1445, 1469 cm$^{-1}$.

RMN-$^1$H ($\sigma$, CDCl$_3$): 8.00 (s, 2H); 3.84 (t, 2H); 3.65 (m, 4H); 2.49 (m, 4H); 2.39 (t, 2H); 2.32 (s, 3H); 1.69 (quint., 2H); 1.55( quint., 2H).

By treating 0.52 g (1.36 mmol) of the previous product dissolved in 15 ml of ethanol, with 37% hydrochloric acid, 0.43 g (75%) of 2-{4-[4-(4,5-dichloro-2-methylimidazol-1-yl)butyl]-1-piperazinyl}-5-hydroxypyrimidine monohydrochloride with a melting point of 212°–6° C. is obtained.

Spectroscopic data: IR (KBr): 1244, 1269, 1363, 1441, 1474 cm$^{-1}$.

RMN-$^1$H ($\sigma$, CDCl$_3$): 11.21 (a, 1H); 9.63 (s, 1H); 8.12 (s, 2H); 4.45 (m, 2H); 3.94 (m, 2H); 3.41 (m, 4H); 3.08 (m, 4H); 2.34 (s, 3H); 1.71 (m, 4H).

Biological Activity

The biological activity is demonstrated in mice, in an exploration test in an illuminated/dark chamber described by B. Costall et al., J. Pharmacology and Experimental Therapeutics, 1992, 262, 90. The experiment is carried out as indicated in the publication mentioned. For a more detailed procedure, B. Costall et al., Pharmacol. Biochem. Behav., 1989, 32, 777 can also be consulted. The compounds are administered intraperitoneally as acute pretreatment and the results indicate the minimal dose at which a significant activity is observed.

| Compound | Minimal dose (mg/kg i.p.) |
| --- | --- |
| Diazepam | 0.125 |
| Ipsapirone | 0.5 |
| Buspirone | 0.125 |
| Lesopitron (E-4424) | 0.0001 |
| Example 1 | 0.000001 |

Taking into account their strong action with respect to their pharmacological properties, the new compounds which are the subject of the invention can be satisfactorily used in human and animal therapy, in particular in the treatment of disorders of the central nervous system, and more particularly for the treatment of anxiety or as tranquillizers.

In human therapy, the administrable dose of course depends on the seriousness of the disease. It can be between 2 and about 20 mg per day. Compounds which are the subject of the invention are administered in the form of tablets, capsules, solutions or suspensions. Two galenic forms for the compounds of the invention are indicated below by way of example.

| Example of formula for tablet | |
| --- | --- |
| Compound of Example 1 | 5 mg |
| Lactose | 60 mg |
| Microcrystalline cellulose | 25 mg |
| Povidone | 5 mg |
| Pregelatinized starch | 3 mg |
| Colloidal silicon dioxide | 1 mg |
| Magnesium stearate | 1 mg |

| -continued | |
| --- | --- |
| Weight of a tablet | 100 mg |
| Example of formula for capsule | |
| Compound of example 1 | 10 mg |
| Polyoxyethylenic glyceride | 135 mg |
| Glycerin behenate | 5 mg |
| Excipient: gelatin | 150 mg |

We claim:

1. 2-[4-(4-azolylbutyl)-1-piperazinyl]pyrimidine derivatives, characterized in that they correspond to the general formula I,

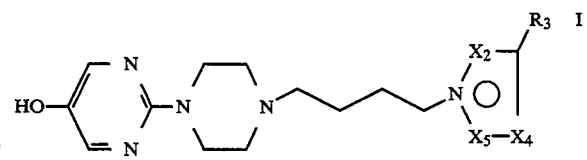

in which X$_2$ represents a nitrogen atom or a C-R$_2$ group, X$_4$ represents a nitrogen atom or a C-R$_4$ group, X$_5$ represents a nitrogen atom or a C-R$_5$ group, and R$_2$, R$_3$, R$_4$ and R$_5$, which are identical or different, represent a hydrogen atom, a halogen, a lower alkyl radical, a nitro radical, a hydroxy radical, an alkoxy radical, a cyano radical, a carboxylic radical, a carboxamide radical, an alkyl carboxylic radical, an aryl radical, a sulphonamido radical, an amino or substituted amino radical, as well as their physiologically acceptable salts.

2. Compounds corresponding to the general formula I according to claim 1, which are chosen from the following:

* 2-{4-[4-(4-chloropyrazol-1-yl)butyl]-1-piperazinyl}-5-hydroxypyrimidine-1-piperazinyl]pyrimidine
* 2-{4-[4-(4,5-dichloro-2-methylimidazol-1-yl) butyl]-1-piperazinyl}-5-hydroxypyrimidine
* 2-{4-[4-(4,5-dichloro-2 methylimidazol-1-yl)butyl]-1-piperazinyl}-5-hydroxypyrimidine hydrochloride.

3. A process for preparing the compounds of general formula I, according to claim 1, characterized in that the following operations are carried out:

* oxidation of 5-benzyloxy-2-thiomethylpyrimidine to yield the corresponding sulphone of formula V,

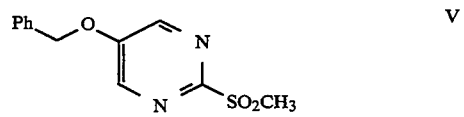

* replacement of the methylsulphonyl radical with a piperazine to yield the compound of formula VI,

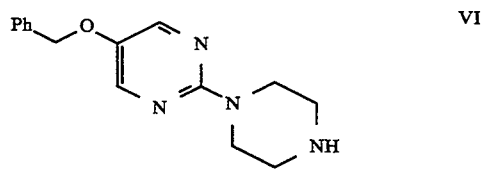

* reaction of compound VI with dibromobutane to yield the corresponding spiro of formula VII,

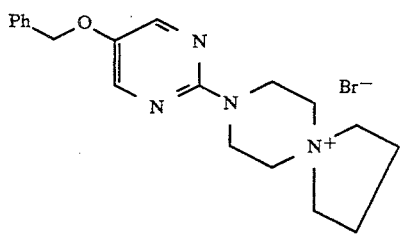

* reaction of 8-(5-benzyloxy-2-pyrimidinyl)-8-aza-5-azoniaspiro[4.5]decane bromide, Compound VII, with an azole of general formula IX

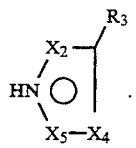

to yield a compound of general formula VIII

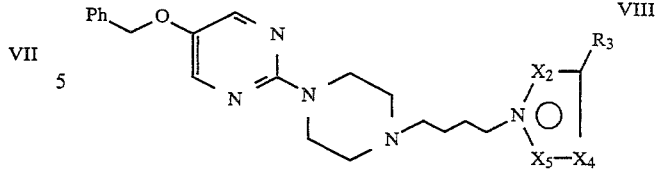

* deprotection of the compound of general formula VIII by hydrogenation of the benzyl group giving rise to the formation of the compound of general formula I, wherein $X_2$ represents a nitrogen atom or a $C-R_2$ group, $X_4$ represents a nitrogen atom or a $C-R_4$ group, $X_5$ represents a nitrogen atom or a $C-R_5$ group, and $R_2$, $R_3$, $R_4$ and $R_5$, which are identical or different, represent a hydrogen atom, a halogen, a lower alkyl radical, a nitro radical, a hydroxy radical, an alkoxy radical, a cyano radical, a carboxylic radical, a carboxamide radical, an alkyl carboxylic radical, an aryl radical, a sulphonamido radical, an amino or substituted amino radical, as well as their physiologically acceptable salts.

4. Pharmaceutical compositions characterized in that they contain, in addition to a pharmaceutically acceptable carrier, at least one compound of general formula I or one of its physiologically acceptable salts, according to claim 1.

* * * * *